United States Patent [19]

Hong Zhang et al.

[11] Patent Number: 5,073,915
[45] Date of Patent: Dec. 17, 1991

[54] DENSITOMETER FOR THE ON-LINE CONCENTRATION MEASUREMENT OF RARE EARTH METALS AND METHOD

[75] Inventors: Cao Hong Zhang; Tao Lun Chang; Pan Yun De, all of Beijing, China

[73] Assignee: Beijing Institute of Nuclear Engineering, Beijing, China

[21] Appl. No.: 503,254

[22] Filed: Apr. 2, 1990

[51] Int. Cl.⁵ ............................................. H03K 23/74
[52] U.S. Cl. ..................................... 378/54; 378/53; 378/85; 378/83
[58] Field of Search .................... 378/53, 51, 54–56, 378/85, 83

[56] References Cited

U.S. PATENT DOCUMENTS

| 3,270,200 | 8/1966 | Rhodes | 250/364 |
| 4,815,116 | 3/1989 | Cho | 378/53 |

FOREIGN PATENT DOCUMENTS

| 2382692 | 11/1978 | France | 378/53 |
| 1017595 | 1/1966 | United Kingdom | 378/53 |
| 2083908 | 3/1982 | United Kingdom | 378/53 |

*Primary Examiner*—Edward P. Westin
*Assistant Examiner*—Don Wong
*Attorney, Agent, or Firm*—Rines and Rines

[57] ABSTRACT

The invention is particularly useful for multi-element solutions wherein successive pairs of X-ray beams are generated and passed through the solution sample corresponding to each of the successive various elements the concentrations of which is to be measured, enabling the on-line concentration measurement of, for example, rare earth elements. Microprocessor control is provided of the presentation of successive X-ray emitting irradiated metal targets to the solution sample and with programming enabling on-line successive measurement of the concentration of each successive element, calibration and storage of such measurements and calculation to eliminate the contribution of other interfering elements from the successive elements to be measured, and display of the successive element concentrations. Applications of the invention may be found, also, in the fields of wet metallurgy for precious metals and less common metals, in the field of petrochemical industry and other chemical engineering applications.

9 Claims, 8 Drawing Sheets

DENSITOMETER FOR THE ON-LINE CONCENTRATION MEASUREMENT OF RARE EARTH METALS AND METHOD

The present invention relates to an analyzer to measure the concentration of various elements in solution by means of X-ray K-absorption (of L-absorption) edge methods. It is especially applicable for the on-line concentration measurement in multielement systems containing rare earth metal mixtures.

BACKGROUND

Rapid concentration measurement of various metal elements in solutions in a rare earth processing plant or in a nuclear fuel reprocessing plant etc. is an important monitoring technique for efficient processing control. In past years, various assay systems based on gamma absorption, X-ray absorption and X-ray fluorescent densitometry have been developed. However, the rapid on-line measurement of the rare earth concentration in multielement systems has not heretofore been satisfactorily developed. In the late nineteen seventies, research institutes of nuclear engineering in West Germany and Japan, initiated development projects to monitor uranium and plutonium during the processing of nuclear fuel reprocessing plants using K-absorption edge, L-absorption edge and X-ray absorption analysis techniques with success. Shotaro Hayashi et al of Japan in 1985 published a paper on a K-absorption edge analyzer, sometimes called densitometer, including the X-ray generator, a sample solution ell. a Ge detector kept and used at low temperature, a multichannel analyzer and a desk top computer. The X-ray generator was composed of an X-ray controller, a high-voltage power supply and a cooling system. This analyzer or densitomer, however, had the disadvantages of structural complexity, high cost of manufacture, and high expense of operation maintenance, and was hardly applicable to the on-line measurement of individual rare earth components in a multi-system rare-earth mixture—the problem underlying the present invention.

OBJECT OF THE INVENTION

The object of the present invention is to provide a new and improved method of and apparatus for the on-line concentration analysis and measurement of individual rare earth metal components in multi-system rare earth mixtures, for example, with the advantages of simple instrumentation, convenient operation, easy maintenance and low cost, and involving a novel method of operation.

Other and further objects will be discussed hereinafter and are more particularly delineated in the appended claims.

UNDERLYING PRINCIPLE AND SUMMARY OF INVENTION

The mass absorption coefficients of a transmitted X-ray may be much greater than those of gamma rays. X-ray absorption has, therefore, a higher susceptibility than the gamma ray absorption and has been widely used in industry for the processing assay and control. Due to the structure of the outer electron energy level of the atoms, the absorption coefficients, in general, decrease with increase of X-ray energy, but will considerably increase when the X-ray energy is a little more than the inner electron ionization energy of an element. Thus, the curves of absorption coefficient vs. energy show step-wise changes at orbital electron energy levels. K-absorption and L-absorption edges are referred to as corresponding to the step-wise changes of K and L orbital electron ionization energies. In other words, an X-ray with energy below these absorption edges will not be absorbed by he electrons in these orbits, and there is a great difference in absorption coefficients between the high side and the low side of the absorption edge. If two X-rays with similar energies are used, one having a little higher energy than the absorption edge of an element and another of a little lower energy than the absorption edge of the element, the mass absorption coefficients of the two X-rays will be considerably different for this specific element only, but not much different for any other element. Therefore, this specific element can be measured effectively using the absorption difference between the two monochromatic X-rays.

The energies of K-absorption edge and the mass absorption coefficient both on the high and the low sides of Fe, Cu, Ag, Sn are listed in Table 1. The present invention for the quantitative analysis of element concentrations is based on the above characteristics of X-ray absorption.

TABLE 1

| Element | K-absorption Edge Parameters | | | |
|---|---|---|---|---|
| | Fe | Cu | Ag | Sn |
| Atomic number | 26 | 29 | 47 | 50 |
| K-absorption Edge (kev) | 7.111 | 8.980 | 25.52 | 29.19 |
| $\mu$ (cm/g) | | | | |
| high side | 431.5 | 296.5 | 55.32 | 44.57 |
| low side | 47.15 | 34.93 | 9.126 | 7.677 |

The analysis of an element involves the measurement of transmitted intensities of an X-ray on the High(H) and Low(L) sides of the edge. It is derived from the Attenuation Law that $$C = K_o + K_1 L_h(I_l/I_h) \tag{1}$$

where C is the element concentration, $I_l$ is the transmitted intensity of X-ray on the low side of the absorption edge, $I_h$ is the transmitted intensity of X-ray on the high side of the absorption edge; and $K_o$, $K_1$ are equation constants (obtained from calibration experiment for the specific subject of analysis.)

In a multielement system, every element contributes to the measurement of the transmitted intensities of the absorption edge for the other elements in the system, so that all of elements interfere with one other. Nevertheless, the difference of absorption coefficients for the interfering element(s) between the two sides of the absorption-edge of the analyzed element is much less, so it is feasible to apply the method underlying the invention to the concentration analysis in multielement systems and to obtain better selectivity and better anti-interference results through calibration. The calibration, in accordance with the invention, is carried out by the numerical method with microprocessor technology using empirical coefficients. Assume, for example, that the component element concentrations in a multielement system are $C_1, C_2, \ldots C_j$. The intensity ratio of the transmitted X-ray on both sides of the absorption edge for the i component is then represented as:

$$R_i = L_n(I_l/I_h)i = f(C_1, C_2 \ldots C_j). \tag{2}$$

The effect of the j element on the absorption of the i element is represented by the empirical calibration coefficient, $K_{ij}$. The concentration of the i element may then be expressed as follows:

$$C_i = K_o + K_{i1}R_1 + K_{i2}R_2 + \ldots K_{ij}R_j \qquad (3)$$

Such a calibration coefficient for each element component is obtained from calibration experiments, and the microprocessor calculation solves the above equations, enabling the subtracting or eliminating of the contribution of other interfering element absorption measurements from the particular element to be measured.

An embodiment of the present invention for practicing the underlying method thereof is composed of an X-ray radiation generator, a moving target mechanism, a sample cell, a probe, a single channel analyzer, an appropriate interface and a microprocessor. The X-ray generator used is preferably one of high intensity, low energy, and long half-life period gamma emission; e.g. an Am generator. The moving target mechanism must be installed with, at least, two targets of different materials, and the number of targets used should be no less than the number of components to be measured. If the number of targets is equal to the number of components to be measured plus one, the influence of the other components in the solution, not to be to measured, will be even smaller. The effect of reading floating and sample thickness will be small, as well. The characteristic X-ray is produced by gamma radiation from the generator striking the target. The probe is preferably composed of a glint crystal; e.g. NaI crystal, a multiplier phototube and a pulse amplifier, as later described in more detail.

DRAWINGS

The attached figures, for purposes of illustrating the practice of the present invention, are as follows.

Figure 5A:
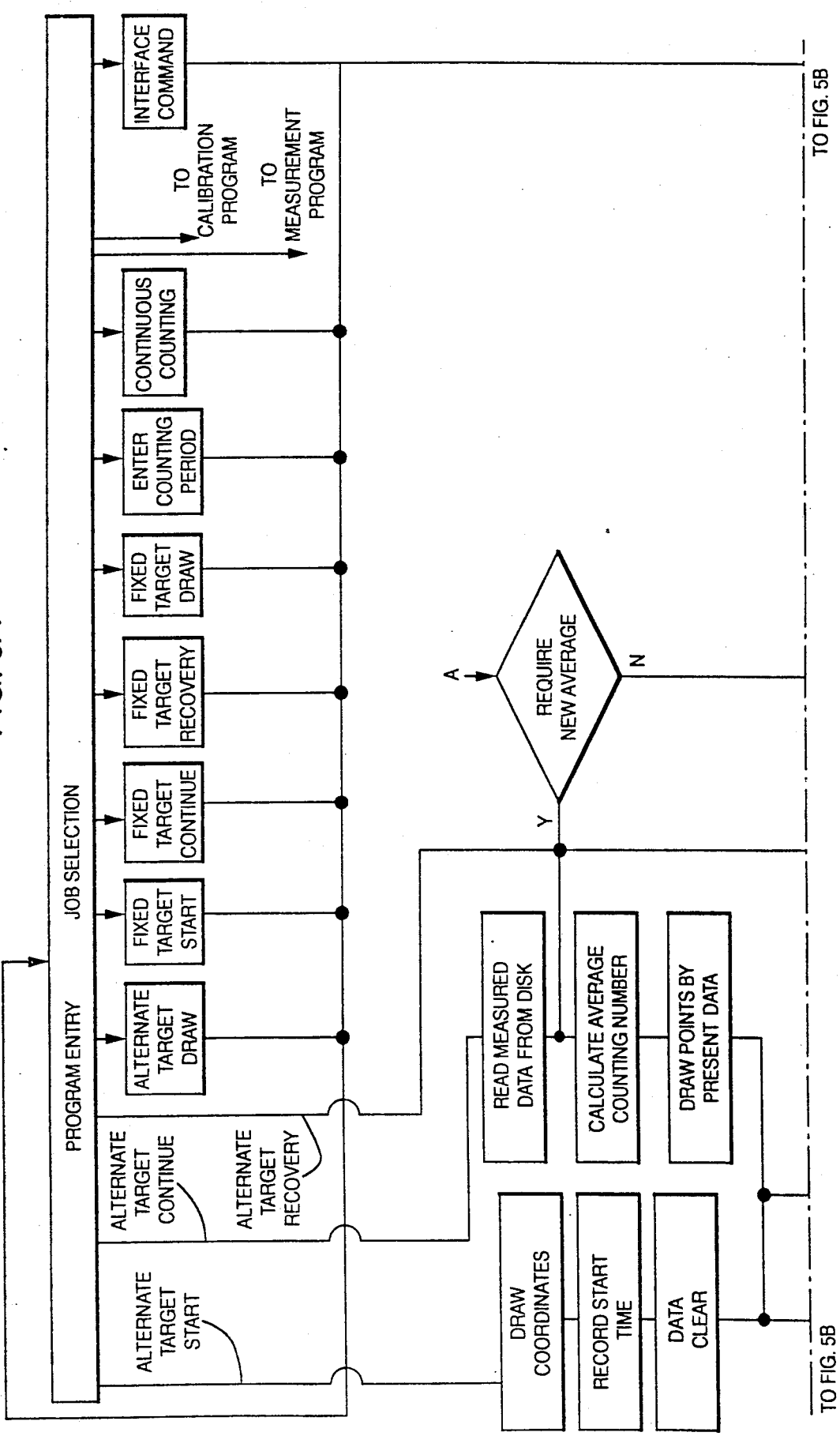
Figure 5B:
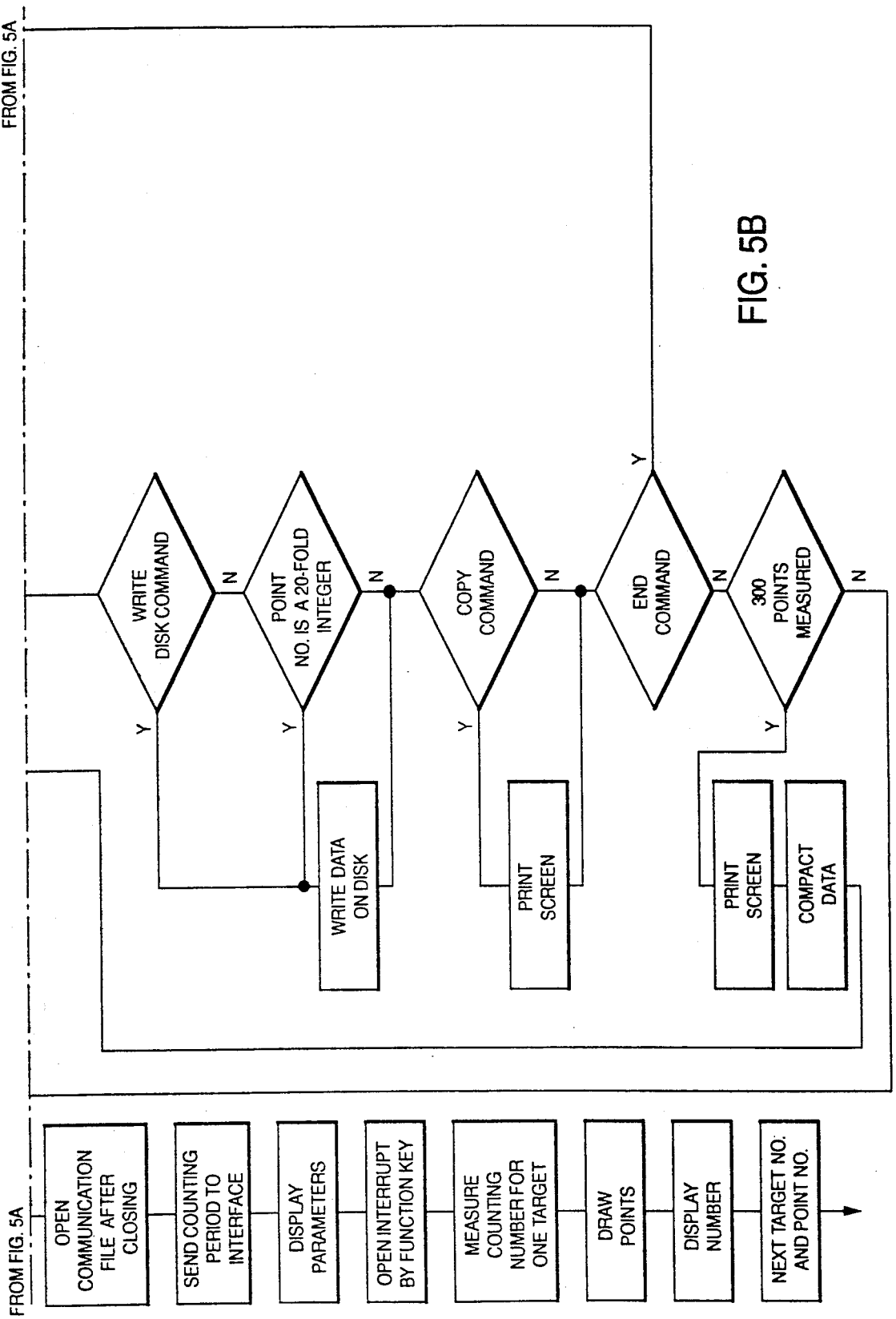
Figure 6A:
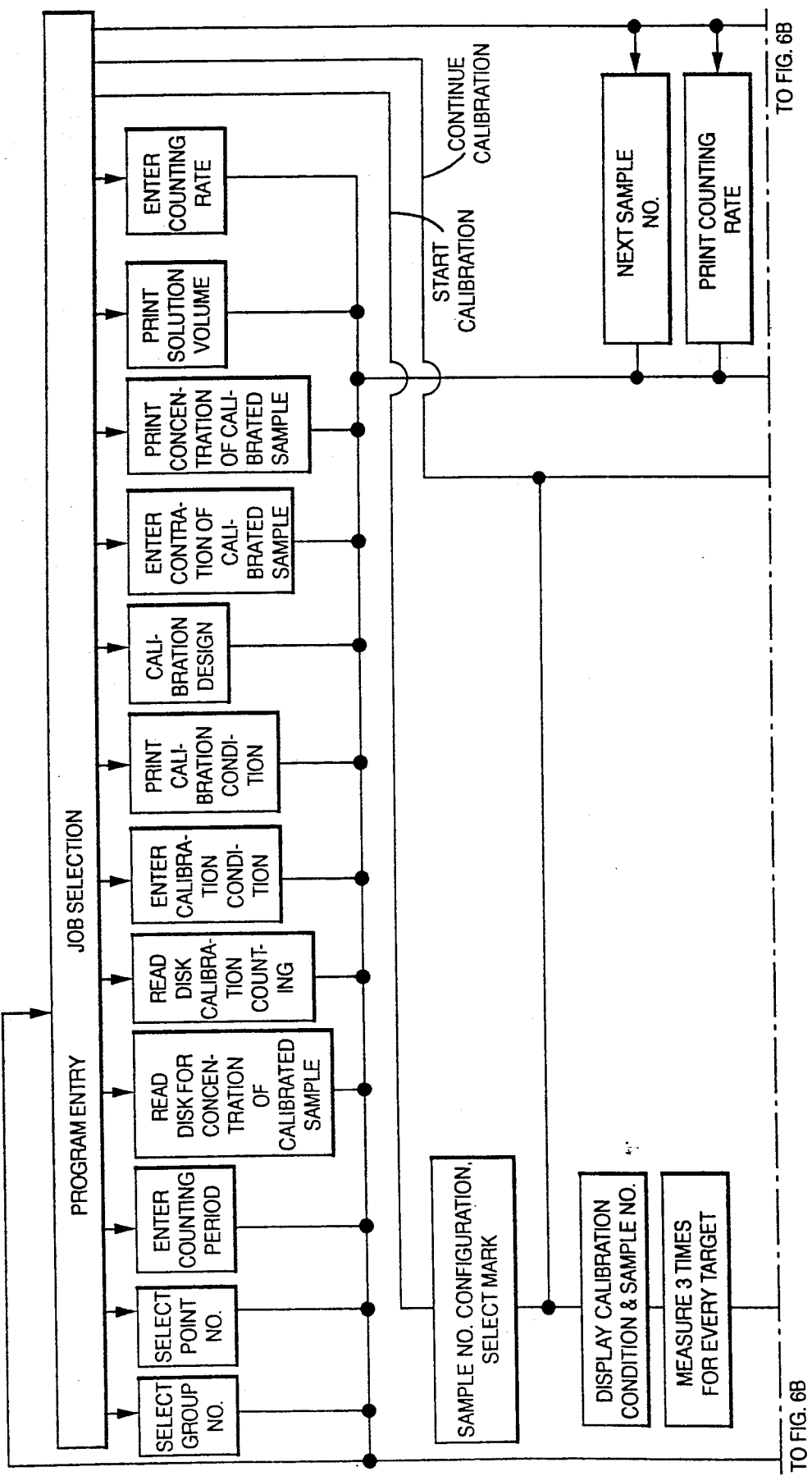
Figure 6B:
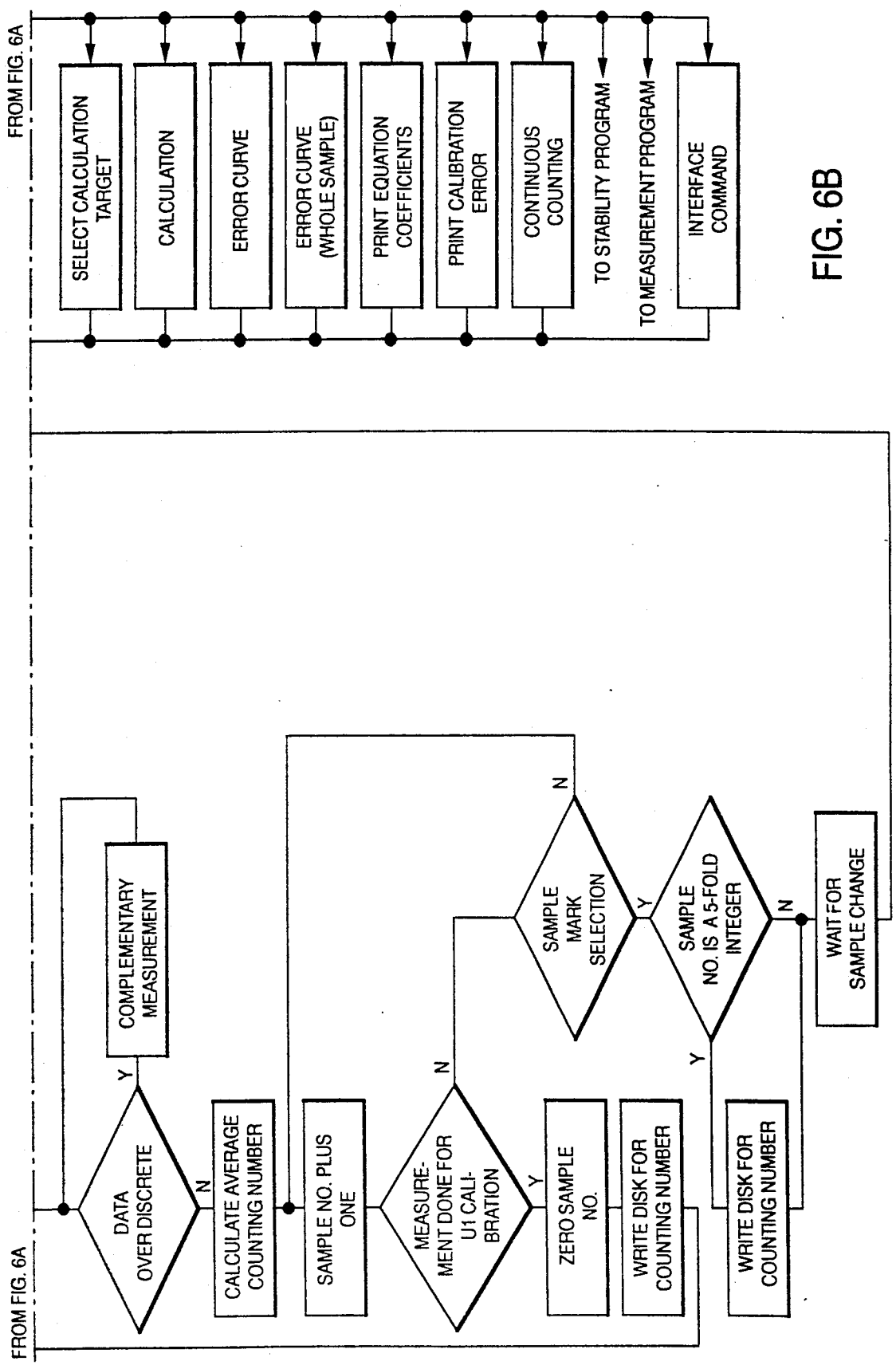
Figure 7A:
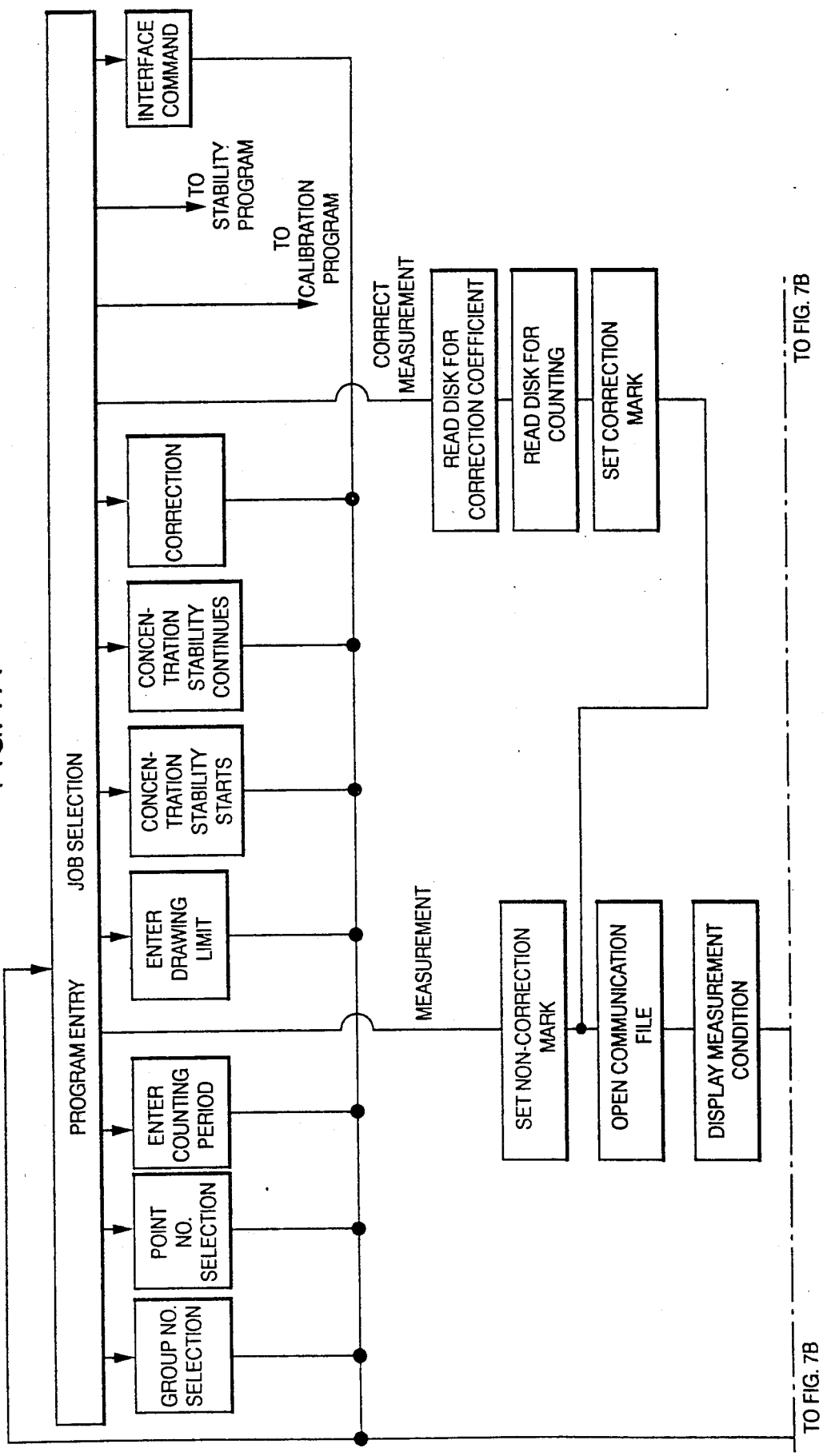
Figure 7B:
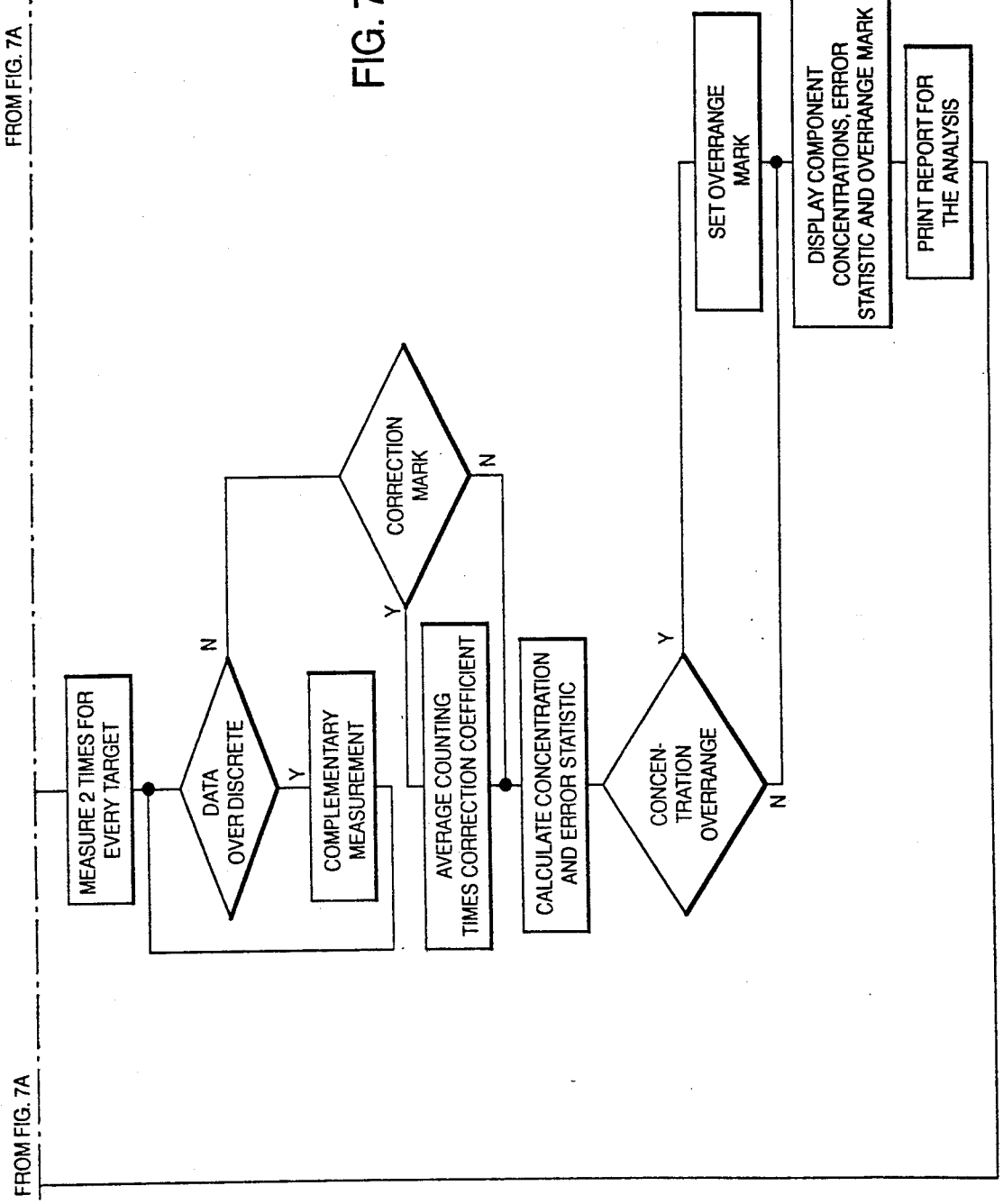

FIGS. 5A-B constitute a detailed flow chart of the program for the microprocessor-assisted system stability examination;

FIGS. 6A-B present a similar flow chart of the calibration program of the microprocessor operation; and FIGS. 7A-B illustrate a flow chart of the measurement program in the microprocessor operation.

INVENTION DESCRIPTION

A more detailed description of a best mode embodiment of this invention will now be described with reference to the attached figures and examples of operational parameters.

Figure 1:
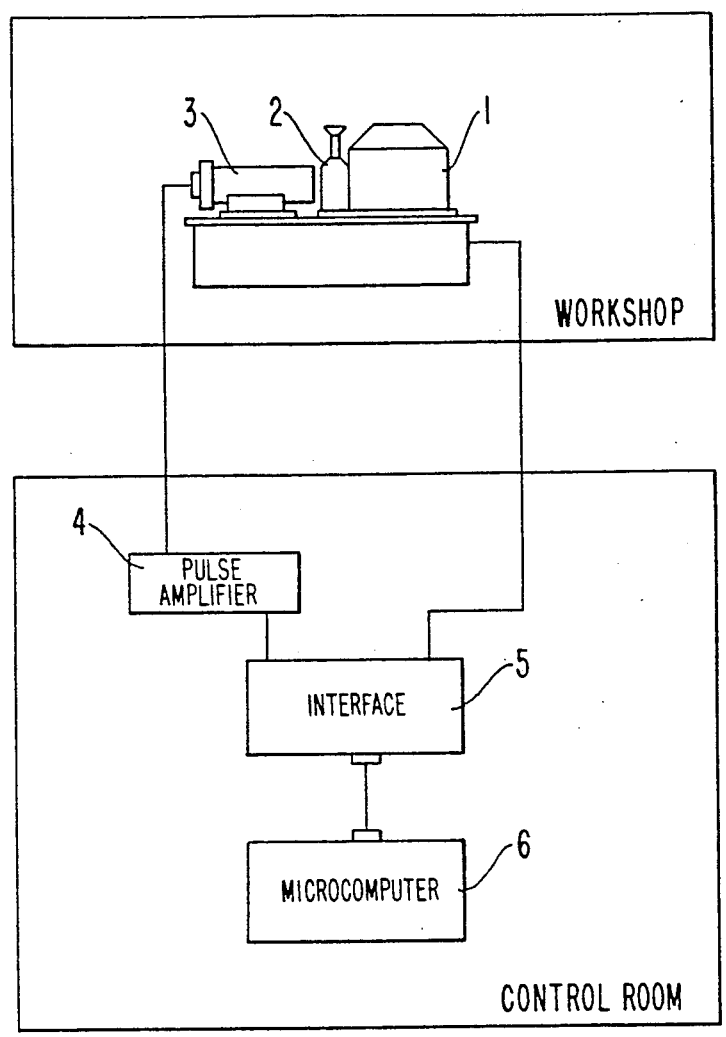
FIG. 1 is the system block diagram of the assay principle for the analysis employed in the invention.

The diagram in FIG. 1 shows the measurement principle of the present invention. The sample cell 2 is fed automatically or manually with the solution of multielements to be measured. Monochromatic X-rays with different energies emitted from the radiation generator—moving target mechanisms 1, later described, pass into the solution and are partially absorbed, with the transmitted X-rays received by a probe 3 and transformed into electrical pulse signals. The probe is preferably a NaI crystal, a multiplier phototube (or proportional counting tube) and a pulse amplifier 4. The pulse counting measured by this single channel analyzer is sent to a microcomputer 6 through an appropriate interface 5, with calculations carried out in the microprocessor 6 according to the above-described equation coefficients pre-calculated to obtain a resultant assay output as more fully explained hereinafter.

Figure 2:
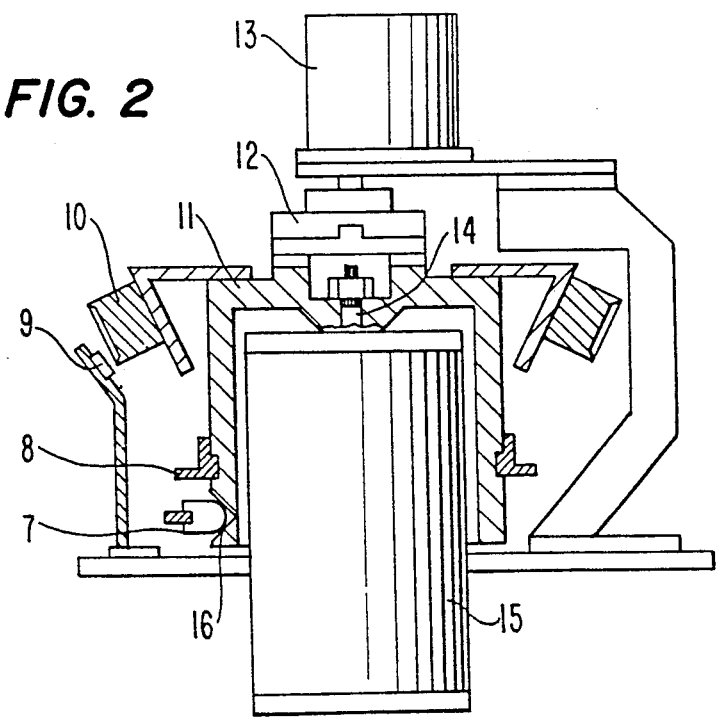
FIG. 2 is a front elevation of the preferred or best mode of radiation generator—rotary target mechanism.
Figure 3:
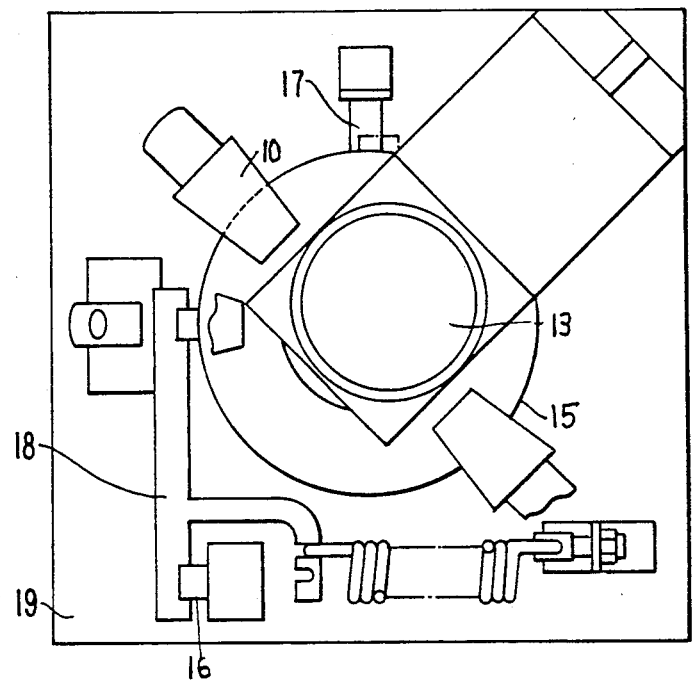
FIG. 3 is a top view of the same.

FIG. 2 and FIG. 3 show the front view and the top view, respectively, of the radiation generator—rotary target mechanism 1 of FIG. 1. A schematic presentation of the radiation generator—translational target mechanism is presented in FIG. 4. The radiation generator—rotary target mechanism employs a reversible motor 13, FIg. 2, through a joint 12, driving a turn table 11 fixed on a main shaft 14 by a step bearing mechanism 15 having accurate positioning. Various targets 10 used to transform energy (or spectrum) are fixed on the turn table 11 and are rotated in circular movement. The interface 5 and microcomputer 6 of FIG. 1 receive the signals from an approach switch 17, FIG. 3, and a position controller 8 on the turn table 11, FIG. 2, determining and controlling the rotation/stop and the position of the turn table, so that the contact 7 at the end of a connecting rod 18, linked with the bed plate 19 by a suspended spring, enables the free slide into a positioning groove 16 on the lateral face of the turn table 11. Therefore, each target 10 is controlled to rotate in succession and to stop in front of the radiation generator 9, FIG. 2. The X-ray transformed from the target 10 with different energies passes the solution to be measured and is then received by the probe 3, FIG. 1.

Figure 4:
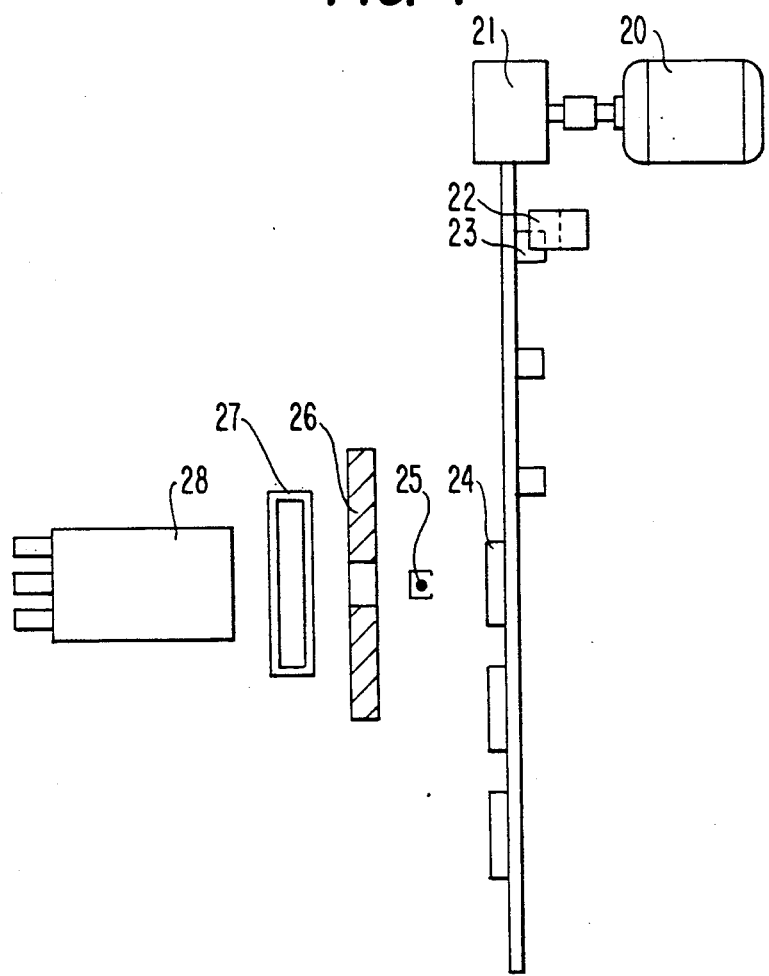
FIG. 4 is a schematic presentation of operation illustrated, for clarity, as in translational target movement instead of rotary as in FIGS. 2 and 3.

In FIG. 4, the operation procedure is illustrated in translational rather than rotary motion, moving the targets labelled 24 instead of 10 as in FIG. 2 and in succession in front of the radiation generator, labelled 25 rather than 9 as in FIG. 2. The motor 20, gear box 21, switch 22, positioner 23, target 24, radiation generator 25, alignment bar 26, sample cell 27 and probe 28 in FIG. 4 function as their corresponding elements in the rotary version of FIGS. 2 and 3.

All the radiation generators in he radiation generator—moving target mechanisms are, as before stated, preferably of Am. The target metals chosen depend on he constitution of the solution to be measured. For the analysis of an individual rare earth component or element in a multielement system, e.g. in the multielement system mixture of rare earth metals, the elements to be measured are arranged in the order of atomic numbers—one target metal being chosen for every two adjacent elements, such that the energy of the characteristic X-ray of the target lies between the absorption edges of the two adjacent elements to be measured. Two more targets may be added. The energy of one target is higher than the absorption edges of all the elements, with the energy of the other lower than those of all the elements. The number of the targets, thus, is equal to the number of elements to be measured plus one. Alternatively, the number of later-added targets can also be one.

For target selection, $\alpha + \alpha$ X-ray, instead of $\alpha$ X-ray, is required, in general; but $\beta$ X-ray is required when the concentrations of the heavy rare earth elements are to be measured. Proper target materials for several rare earth elements to be measured are listed in Table 2. It should be noted that there is a common boundary between the element to be measured and the target material when the Table 2, below, is used.

TABLE 2

| Element to be Measured | La | Ce | Pr | Nd | Sm | Eu | Gd |
|---|---|---|---|---|---|---|---|
| Target | Nd | Sm | Eu | Gd | Tb or Dy | Ho | Er | Tm |

The sample thickness, i.e. the width of the sample cell, must be appropriate. The bigger the sample thickness in the linear error region, the larger the concentration reduction coefficient and, thus, the smaller the error of the measurement. Too thick a sample will change the spectrum due to the excessive absorption, resulting in non-linear error. The higher the concentration and the more the concentration varies, however, the smaller the optimum sample thickness. The optimum sample thickness can be determined experimentally. The error in the linear region is not very sensitive to the sample thickness, so that it is not necessary to optimize the sample thickness by experiments for each analyzed point. Approximate thickness may be allowed, but not so large as to fall in the non-linear error region. The appearance of the relatively large non-linear error may be found from a deviation error curve when the errors are usually very large, and may simultaneously vary with the maximum concentration range. The sample thickness must be reduced, however, when such occurs.

The control system of the present invention, as before stated, is composed of an interface 5 and microprocessor 6. The microcomputer or microprocessor 6 may be the model IF-800 or PC-9801 computer depending upon the requirements of the measurement. Twenty functions may be programmed and shown on the screen; e.g. input the names of the analyzed points; input the instrumentation condition; print the concentration of the calibrated sample; select the measurement target; calibrate the measurement; select the calculation target; calculate and print the table of the equation coefficients; print the table of deviation errors; and measure the samples etc. The operator, as requested, may choose any one of these functions by entering the same interactively, with the interface enabling control of the measurement apparatus upon receipt of the command from the microprocessor, and returning a feedback signal to the microprocessor after execution of the command, indicating a readiness state.

Reference is made to the detailed flow chart functions for target start, movements, recovery and corresponding probe counting under the control of the microprocessor program as outlined in FIGS. 5A and 5B, enabling stable examination. A detailed calibration program and appropriate calculation series is presented in the flow charts of FIGS. 6A and 6B; and measurement and correction sequences are detailed in he flow charts of FIGS. 7A and 7B.

In summary, however, the calibration method steps for the analyzer are principally as follows:
 (1. Determine the application area. If the analyzer is used for processing control and analysis in plant, all the samples should be divided into many series with corresponding numbers and names given in order to determine the number of the measured elements and the fluctuation range of the concentration for each element in the production process.
2. Determine the amount of the standard sample made for every series.
3. After the standard samples are made, various data will be sent to the microprocessor and be stored on a disk with the corresponding numbers and names by the interactive operation above-referenced. The measurement process begins with pouring the number 1 sample into the sample cell 2. The microprocessor, so long as the calibration program is executed, shall automatically start the measurement and the counting at regular intervals for each target, in order. The process is repeated three times, so that the calculation result of the average counting rate and the logarithm of the counting rates will be obtained.

The present invention enables assay of individual element concentrations in complex component systems, either on-line or in he laboratory, and at every controlling point of the processing. The analyzer, as before stated, is especially applicable for fast analysis of the element concentrations in the rare earth mixture solutions containing La, Ce, Pr, Nd, Sm, Eu, Gd, Y etc. in a rare earth processing plant. As above described, the stability examination program for the whole system is outlined in FIGS. 5A and 5B; the calibration program in FIGS. 6A and 6B; and the assay program in FIGS. 7A and 7B. The calibrated coefficients for empirical correction are stored on a disk for long term use, with the number of equations stored for the calculation of concentrations being unlimited. The samples for recalibration can be made any time in case the range of the component and concentration at the analyzed point changes. The routine operation of the analyzer for the measurement is also very simple. One only need to pour the sample to be measured into the sample cell with a given thickness and enter the command according to the measurement condition calibrated, and the microprocessor will control the measurement automatically and give the calculation results. Only 3-5 minutes are needed in practice to measure the element concentration for the samples containing a few elements; up to ten minutes for the samples containing more elements.

For the concentration measurement of a multi-point, multi-component system, such a microprocessor and interface have been used to control many (e.g. twelve) primary systems, each composed of radiation generator—moving target, sample cell and probe, and single channel analyzers to measure the concentration of every component at every point continuously on-line. All the apparatus were, upon measurement, operated simultaneously under the control of the microprocessor. The microprocessor collected the data at regular intervals, calculated the result, and stored the same on a disk, displaying the corresponding curves of the component concentration on the screen, and providing instructions for the production processing so that the operating parameters could be corrected in time.

The present invention possesses the following advantages:
1. Flexibility, versatility and the prospects for wide application; the analyzer being, in general, applicable to all elements having moderate or higher atomic numbers in unary systems or in complex system.

2. This technique has more advantages than other conventional methods of analysis when it is used for liquid samples. The samples need not be pretested; the speed is much faster than that of X-ray fluorimetry or volumetry; and the samples will not be damaged. This technique is, therefore, suitable for processing control and on-line monitoring in the field.

3. The processing control and data analysis are simple and convenient due to the application of the microprocessor technology. The equipment can be easily handled so that ordinary operators may master it in a short time.

4. A single channel spectrometer under microprocessor control is used for multi-channel measurement, with sufficient resolution and measurement accuracy, and reduced manufacturing cost. The present analyzer, moreover, is more applicable to the production field and the analysis station, being useful also in the fields of wet metallurgy for precious metals and less common metals, in the field of petrochemical industry, and other chemical engineering applications.

Further modifications will occur to those skilled in this art, such being considered to fall within the spirit and scope of the invention as defined in the appended claims.

What is claimed is:

1. A method of on-line concentration measurement of multi-elements in solution, that comprises, generating successive pairs of similar energy monochromatic X-ray beams, each pair of beams having one of slightly higher and the other beam of slightly lower energy than the K or L orbital electron ionization energy absorption edge of one of the elements in solution, the concentration of which element is to be determined,; said generating comprising impinging radiation from a source upon successive different metal targets selected to correspond to the respective pairs of similar energies corresponding to each particular element the concentration of which in solution is to be determined, with the metal of the successive targets being selected for every two adjacent elements in the multi-element solution, arranged in order of atomic numbers, such that the energy of the X-rays characteristic of of each target lies between the said absorption edges of two adjacent elements in solution; successively relatively moving said targets past the radiation source and in position to pass the target-generated rays through the solution; measuring the absorption difference by the successive elements in solution to the corresponding pair of X-ray beams to determine the concentration of that element in the solution; applying the measured absorption differences to microprocessor means while programming the same to control the target movement and for enabling each of on-line successive measurement of the concentration of each successive element in solution, calibration and storage of such measurements and calculation to eliminate the contribution of other interfering elements from the successive elements to be measured, and display of the successive element concentrations.

2. A concentration analyzer for on-line concentration measurement of a mixture of multi-elements in one or more solution samples having, in combination, means for generating successive pairs of similar energy monochromatic X-ray beams each pair of beams having one beam of slightly higher energy and the other beam of slightly lower energy than the K or L orbital electron ionization energy absorption edge of one of the elements in solution, the concentration of which element is to be determined; the generating means comprising means for impinging radiation upon successive different metal targets selected to correspond to the respective pairs of similar energies corresponding to each particular element the concentration of which in said solution samples is to be determined, with the metal of the successive targets being selected for every two adjacent elements in the multi-element mixture in the solution, arranged in order to atomic numbers such that the energy of the X-rays characteristic of each target lies between the said absorption edge of two adjacent elements in the solution; means for successively relatively moving said targets past the radiation impinging means and in position to pass the target-generated rays through the solution; means disposed with respect to the solution for measuring the absorption difference by the respective element in solution to the corresponding pair of X-ray beams to determine the concentration of that element in the solution; and microprocessor means responsive to the measuring means and having means for controlling the target movement and programming means for enabling each of on-line successive measurement of the concentration of each successive element, calibration and storage of such measurements and calculation to eliminate the contribution of other interfering elements from the successive elements to be measured, and display of the successive element concentrations, thereby enabling automatic continuous-on-line measurement of the successive elements.

3. A concentration analyzer as claimed in claim 2 and in which said means to measure the absorption difference comprises pulse-generating NaI probe means connected by single channel analyzer means with the microprocessor means.

4. A concentration analyzer as claimed in claim 2 and in which the radiation impinging means comprises an Am source.

5. A concentration analyzer as claimed in claim 2 and in which the multi-element solution sample contains metal ions selected from the group consisting of Fe, Cu, Ag and Sn.

6. A concentration analyzer as claimed in claim 5 and in which the targets are selected to generate $\alpha + \alpha$ X-rays.

7. A concentration analyzer as claimed in claim 2 and in which the multi-element solution samples contain rare earth mixtures selected from the group consisting of La, Ce, Pr, Nd, Sm, Eu, Gd and Y.

8. A concentration analyzer as claimed in claim 7 and in which the targets are selected to generate $\beta$ X-rays.

9. A concentration analyzer as claimed in claim 2 and in which the number of targets is equal to the number of elements plus one.

* * * * *